United States Patent [19]
Panyard

[11] Patent Number: 5,634,940
[45] Date of Patent: Jun. 3, 1997

[54] THERAPEUTIC STRUCTURE AND METHODS

[76] Inventor: Albert A. Panyard, 53470 Andrew Cir., New Baltimore, Mich. 48047

[21] Appl. No.: 571,475

[22] Filed: Dec. 13, 1995

[51] Int. Cl.$^6$ .................................................. A61F 7/00
[52] U.S. Cl. ........................ 607/104; 607/108; 607/114
[58] Field of Search ..................... 607/104, 108–112, 607/114

[56] References Cited

U.S. PATENT DOCUMENTS

| | | | |
|---|---|---|---|
| 5,324,319 | 6/1994 | Mason et al. | 607/104 |
| 5,372,608 | 12/1994 | Johnson | 607/104 |
| 5,486,206 | 1/1996 | Avery | 607/104 |

*Primary Examiner*—Angela D. Sykes
*Assistant Examiner*—Ryan Carter

[57] ABSTRACT

Structure for and method of therapeutic treatment of a body portion to relieve swelling and pain and facilitate healing of injuries, wounds and incisions. The structure includes a shield adapted to be placed in intimate surface to surface contact with the body portion, a regulator for passing a fluid through the shield at a regulated temperature and/or flow rate, a control for controlling the flow and temperature of the fluid and a temperature sensor for modifying the temperature and flow of the fluid in response to monitored temperature which may be the temperature of the body portion. The shield is constructed of an inner and outer elastomeric member, at least the inner member of which is in the exact form of the body portion to be treated, which inner and outer members are sealed together to form a pocket, a tube in the form of the body portion within the pocket, and a gelatinous substance within the pocket positioned between the tube and inner member. The inner and outer members may be directly molded on castings of the body portion and the tube may be coiled and adhered to the inner surface of the outer member. In use, the shield is positioned over a body portion to be treated in intimate surface to surface contact therewith, and fluid (water} is passed through the tube from the regulator at a flow rate and having a temperature controlled by the controller modified by the monitored temperature.

20 Claims, 3 Drawing Sheets

THERAPEUTIC STRUCTURE AND METHODS

BACKGROUND OF THE INVENTION

1. Field of the Invention

The invention relates to a structure for and method of therapeutic treatment of a body portion requiring maintaining the body portion at a programmed temperature and a method of making the structure.

More specifically, the invention relates to a therapeutic device including a shield for application to a body portion in intimate surface to surface contact therewith and means for regulating the temperature of the shield by passing a fluid therethrough having a temperature maintained in accordance with a predetermined program and/or the temperature of the body portion. The invention also specifically refers to a method of manufacturing the device and the method of therapeutic treatment of the body portion with the device through the application of the shield of the device to the body portion in intimate surface to surface contact therewith.

2. Description of the Prior Art

In the past, devices have been known for cooling or heating a body portion such as a knee, ankle, neck or the like to reduce swelling, to promote healing and to relieve pain. Such devices include ice packs, common splints, neck braces, cooled or heated wraps and the like. They also include devices for cooling or heating of a body portion in accordance with the type of injury and/or surgery and/or the time during a healing cycle of the body portion.

The more sophisticated of the prior art devices sometimes are provided with passages therein, through which a liquid from a fluid reservoir is passed to either heat or cool a body portion. With such devices, the fluid has usually been pumped at an inconsistent temperature or has been circulated without pumping, using a thermosiphon principle.

The known devices of the past are inadequate since they do not conform intimately to the surface of the body portion to be treated, the temperature of which it is desired to control, whereby they are inefficient. Also, they are uncomfortable in that they are not initially molded to the body portion to conform to the shape of the body portion to be temperature controlled and are bulky. In addition, with prior known devices, temperature control has been non-uniform and inconsistent due to poor surface to surface contact between the shield of the device and the body portion.

One such device is found in U.S. Pat. No. 5,411,542. The device as disclosed in this patent is flat and is adapted to be wrapped around ankle and foot body portions. The device has straps for securing it in place, and passages for the passing of fluid therethrough. As indicated above, this device is deficient in that it is not constructed to be in close surface to surface contact with a body portion the temperature of which it is desired to control, and no temperature control means are shown. In fact, no means for circulating the fluid is shown in this disclosure.

The device shown in U.S. Pat. No. 5,411,541 teaches pumping of fluid through a fluid therapy device and control of the fluid temperature. It does not, however, suggest control of the temperature of the body portion in accordance with the flow of the fluid and/or the temperature of the body portion.

The U.S. Pat. No. 5,372,608 merely teaches a thermosiphon employed for circulating fluid through the therapeutic device shown, and does not suggest any control of the temperature of the fluid other than to have frozen particles such as ice in the fluid container.

U.S. Pat. No. 4,745,922 shows a substantially conventional neck brace which is not intended to be in intimate surface to surface contact with the body portion it is intended to immobilize. While U.S. Pat. No. 4,745,922 teaches tubing with heating or cooling fluid passing therethrough, and other articles such as a compress and an ice bag placed in the brace next to the body portion to be treated, no adequate temperature control means is disclosed. Again, the device is strapped to the patient.

None of these prior art devices disclose a shield molded in the shape of a body portion to be treated so as to be in intimate surface to surface contact therewith. Further, these prior art devices do not teach a fluid carrying tube coiled in the shape of a body portion having adjacent portions in surface to surface contact with each other or a gelatinous substance hermetically sealed in a pocket with the coiled tube for the purpose of maintaining the shield in intimate surface to surface contact with the body portion.

SUMMARY OF THE INVENTION

Accordingly, there is a need for therapeutic devices for programmed cooling and/or heating of any portion of the body. The devices should include a part capable of being placed in intimate contact with the surface of a body portion and should be capable of maintaining the temperature of the body portion in a predetermined program and be responsive to the temperature of the body portion. The device of the present invention includes these features due to its unique construction and methods of manufacture and use.

In accordance with the present invention, the therapeutic device comprises a shield which includes an inner member molded of flexible material to an exact mirror image of a body portion to be treated and an outer member molded to at least the approximate configuration of the body portion. A coiled tube, shaped to approximate the body portion shape, through which fluid may be passed is secured to the outer member on the inner surface thereof with adjacent tube portions in surface to surface contact with each other. A gelatinous substance is positioned between the coiled tube and the inner surface of the inner member, which serves to hold the outer surface of the inner member in intimate contact with a body portion to be treated.

In a preferred method of manufacture of the shield of the therapeutic device of the invention, a cast of the body portion to be treated is made directly from the body portion, an image in the exact shape of the body portion is then made in the cast. Then the inner member of the therapeutic device is produced by molding a thin layer of flexible elastomer on the image of the body portion.

A subsequent slightly larger than life second image of the body portion is made and the outer member of the shield of the therapeutic device is produced again by molding a relatively thin layer of an elastomer over the larger image of the body portion.

Both the images of the body portion may be made by first reducing the cast of the body portion to be treated to mathematically exact digital electric signals representative of the surface of the body portion which are stored and later retrieved and used to reproduce an exact body portion image which is life size, larger or smaller than life size in accordance with known technology.

A tube is wound so as to substantially conform to the inner surface of the outer member with the ends of the tube extending out of the outer member for attachment to a fluid reservoir or the like.

A gelatinous substance is then placed between the inner surface of the inner member and the tube which tube is secured to the inner surface of the outer member, and the inner and outer members are sealed together about their periphery. The seal may be a hermetic seal.

The complete shield is then connected through the ends of the tube to a fluid reservoir including means for heating or cooling the fluid therein and/or regulating the flow of fluid from the reservoir through the tube and back to the reservoir, and a control is connected to the fluid reservoir which is responsive to structure for sensing the temperature of the body portion to be treated.

In use, the therapeutic device of the invention is placed over a body portion, the temperature of which it is desired to control, and fluid is passed through the tubing at a controlled temperature and/or controlled fluid flow to maintain the body portion at a programmed variable temperature or a constant temperature, either of which may be responsive to the actual temperature of the body portion to be treated.

In such method of use, the outer surface of the inner member of the shield is held in intimate surface to surface contact with the body portion to be treated due to the flexible nature of the elastomer of which it is made and the omni-directional forces applied thereto through the gelatinous substance under the weight of the device and the fluid passing therethrough and/or external pressure applied to the shield.

Temperature transfer from the fluid in the tube through the tube, gelatinous substance and inner member of the therapeutic device is enhanced by the tube sections being in contact with each other and with a large portion thereof exposed to the gelatinous substance and in particular with the gelatinous substance being in intimate contact with the inner surface of the inner member in a hermetically sealed shield.

Accordingly, with the device of the invention, the temperature of a body portion may be controlled as desired without discomfort to the patient. The control of the temperature of the body portion may be used to reduce swelling as in sprains or the like during either short or long term treatment of an injury with cold fluid flowing through the tube. The devise of the invention can be used continuously for hours or days without interruption, without discomfort or injury to a patient. The cold fluid flowing through the tube may also be used during treatment of an injury and as post-operative pain control short or long term therapy. Further, in certain treatments, the body part may be warmed to promote healing by passing heated fluid through the temperature control therapeutic device.

DESCRIPTION OF THE PREFERRED EMBODIMENT

Figure 1:
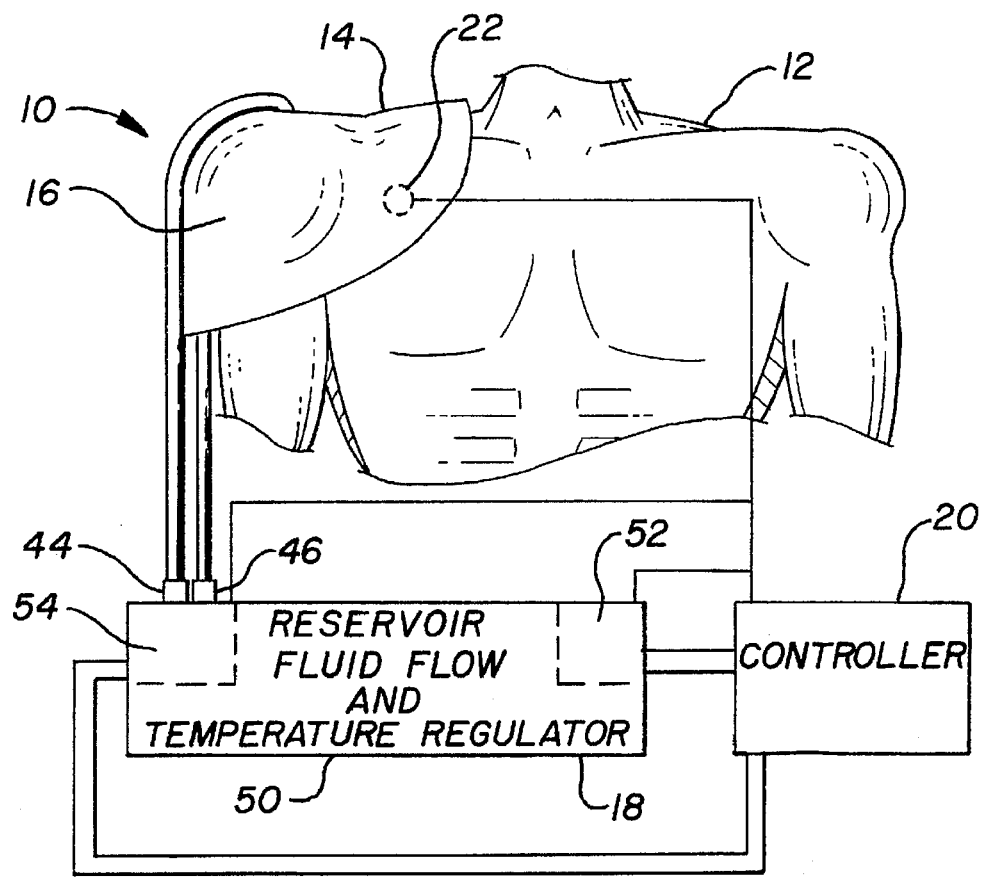
FIG. 1, is a diagrammatic front view of a portion of a patient with the shield of a therapeutic device constructed in accordance with the invention positioned on the right shoulder of the patient, which shield may be constructed and which device is adapted to be utilized in accordance with the methods of the invention.

As shown best in FIG. 1, the therapeutic device 10 of the invention has been formed to treat the right shoulder 16 of a patient 12. The therapeutic device 10 includes a shield 14 constructed in the form of the shoulder 16 of the patient 12. The device 10 further includes a reservoir, fluid flow and temperature regulating structure 18, a controller 20 and a temperature sensor 22.

Figure 2:
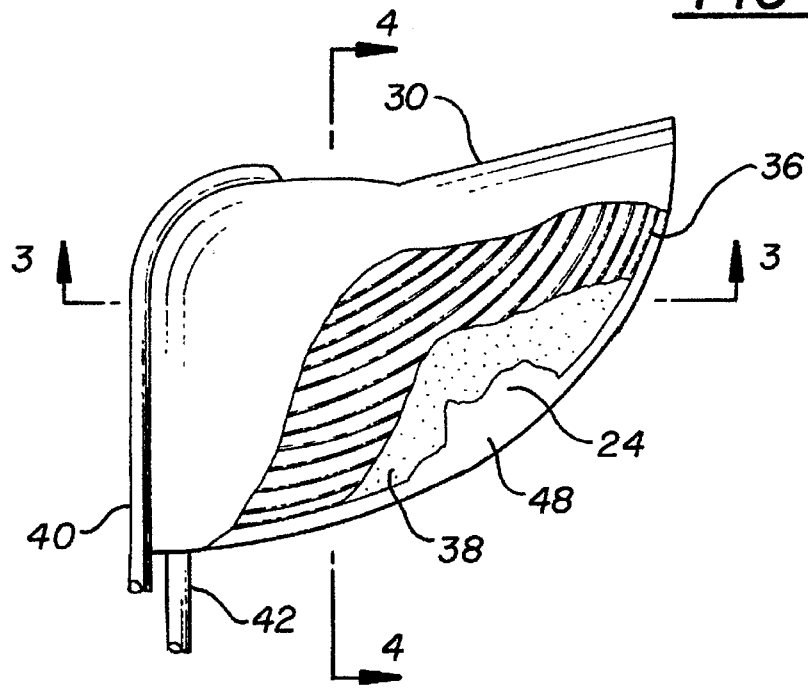
FIG. 2, is an enlarged front view of the shield of the therapeutic device illustrated in FIG. 1, partly broken away to show the inner and outer members and the tube and gelatinous substance of the shield.
Figure 3:
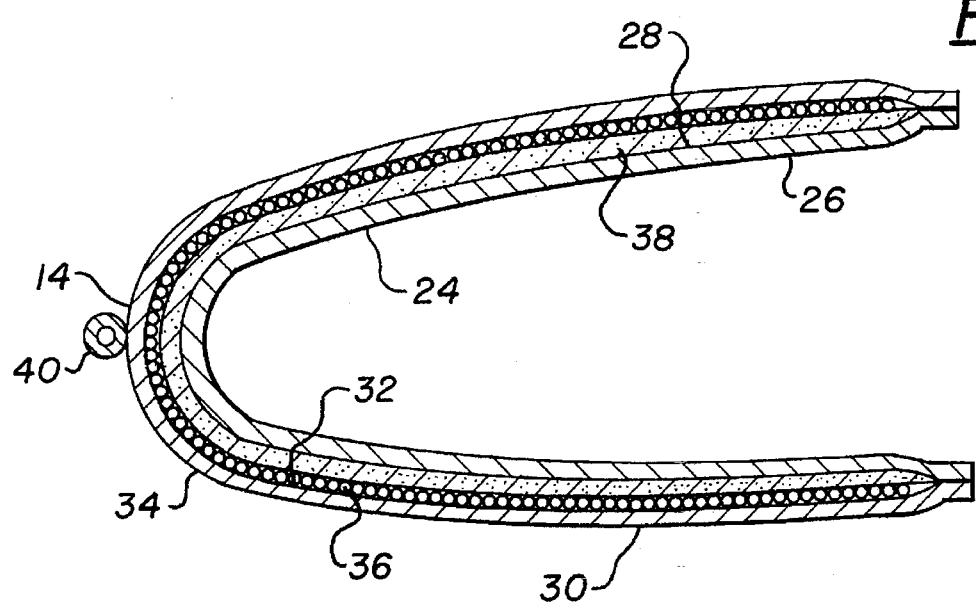
FIG. 3, is an enlarged section view of the shield of the therapeutic device illustrated in FIGS. 1 and 2, taken substantially on the line 3—3 in FIG. 2.
Figure 4:
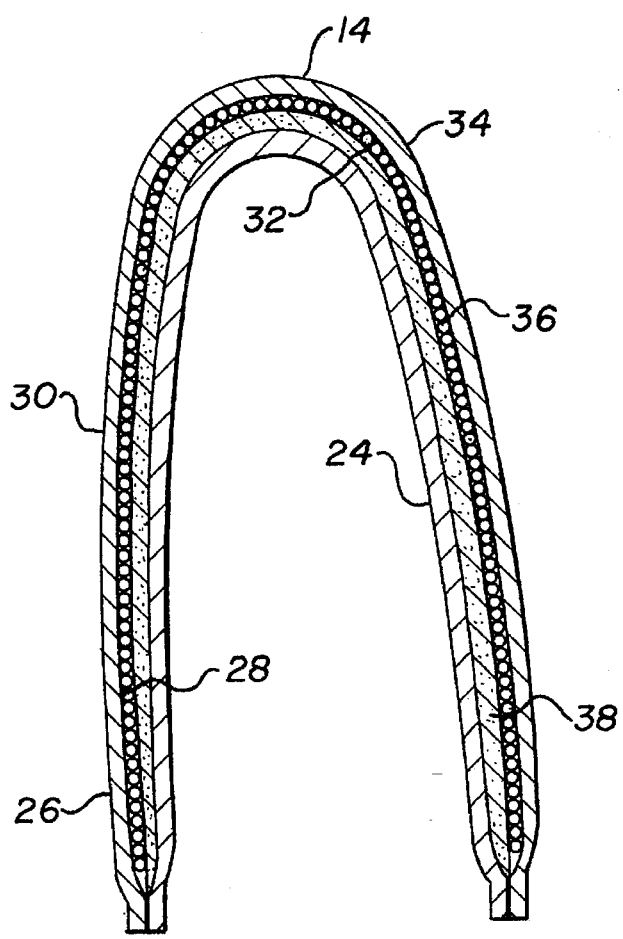
FIG. 4, is another enlarged section view of the shield of the therapeutic device illustrated in FIGS. 1 and 2, taken substantially on the line 4—4 in FIG. 2.
Figure 5:
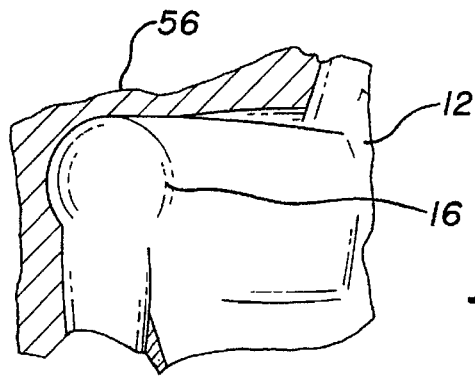
FIG. 5, is an illustration of the first step in producing the shield of the therapeutic device of FIG. 1, illustrating a cast produced on a body portion of a patient.
Figure 6:
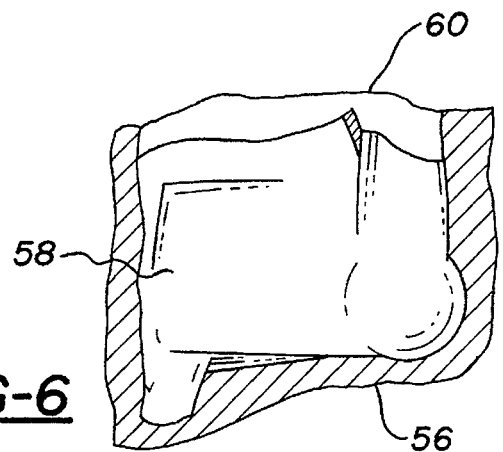
FIG. 6, is an inverted view of the cast shown in FIG. 5, with an exact image of the patient's body portion cast therein.

The shield 14, as shown in more detail in FIGS. 2–4, includes an inner member 24 molded of a thin, flexible elastomer, or like polymer, to the exact shape of a patient's body portion, the shoulder 16. The inner member 24 has an outside 26 and an inside 28, as shown best in FIGS. 3 and 4.

The inner member 24 is preferably constructed of an elastomer such as a block copolymer or vulcanizate, which has a memory property. Other materials may be used for the inner member 24, but should have a high degree of flexibility, a memory property and be capable of being molded by any of a number of molding processes to the exact negative image of the shape of a human body portion, such as shoulder 16.

The outer member 30 also has an inner surface 32 and an outer surface 34. The outer member 30 is formed in the approximate form of the shoulder 16 of the patient 12, but is slightly larger than the inner member 24 to accommodate coiled tube 36 and a gel, gelatinous or gelatinoid substance 38 in the pocket 48 between the inner and outer members 24 and 30.

Again, the outer member may be constructed of an elastomer and should have a high degree of flexibility and a memory property. Outer member 30 also preferable has an insulating property to slow heat transfer therethrough with the shield 14 in use.

In the shield 14 of the therapeutic device 10, the tube 36 is coiled to form the general shape of the shoulder 16 and is secured as by a suitable adhesive or the like to the inner surface 32 of the outer member 30. The adjacent coiled portions of the tube are in surface to surface contact with each other as shown best in FIG. 2 to promote fluid temperature transfer therebetween, and thus uniform temperature throughout shield 14.

The ends 40 and 42 of the tube 36, also constructed of an elastomer, extend out of the shield 14 and are connected to the reservoir, fluid flow and temperature regulator 18 through appropriate connectors 44 and 46.

As shown in FIG. 2, the tube 36 may be a one quarter inch tube and as coiled in the shape of a body portion to be treated and secured to the outer member 30 of shield 14 is substantially kink proof.

The gelatinous substance 38 of the shield 14 is positioned between the tube 36 and the inner shield member 24 and may be a silica gel. The gel must be soft and pliable at the temperatures of the shield and may be free in the pocket 48 between the inner and outer members 24 and 30 or may be incased in a thin pliable sac within the pocket.

The inner member 24 is heat sealed about its periphery to the periphery of the outer member 30 of the shield 14, with tube 36 and gel 38 being the only material therebetween to complete the shield 14, constructed as shown in FIG. 2. The pocket 48 between the inner member 24 and outer member 30 may if desired be vacuum sealed.

Gelatinous substance 38 serves to cause the inner member 24 of the shield 14 to maintain a position in intimate surface to surface contact with the shoulder 16 of the patient 12 under the weight of the shield 14 and any fluid passing therethrough and/or pressure applied to the shield 14, due to the omnidirectional forces applied to the inner member 24 of the shield 14 through the gelatinous substance. The gelatinous substance 38 makes up for any minor body portion to shield surface variation by deforming the shield member 14 to conform exactly to the surface of the body portion to be treated.

Due to fluid temperature transfer from the tube 36 which is in intimate contact with the gelatinous substance 38 and the contact of the gelatinous substance 38 with the inner member 24 of the shield 14 and the absence of other material such as air in the shield, a high degree of uniform fluid temperature transfer is maintained between a fluid in the tube 36 and the patient's shoulder 16.

The reservoir, fluid flow and temperature regulator 18 includes a reservoir 50 for a liquid such as water, a temperature control 52 and a fluid flow control 54. The temperature control 52 includes means for cooling and/or heating the fluid in the reservoir 50, in accordance with electrical signals from the controller 20. The flow control 54 includes means for controlling the quantity of fluid flowing through the tube 36 per unit time in accordance with electrical signals received from the controller 20.

The controller 20 is an electronic device, preferably digital, which will control the reservoir, fluid flow and temperature regulator 18 to regulate the temperature of the fluid in the reservoir and thus the temperature of the liquid flowing through the tube 36. The controller 20 further controls the quantity of fluid passing through the tube 36 per unit of time from the regulator, thereby further regulating the temperature of the shield 14 of the therapeutic device 10.

Further, in accordance with the invention, the controller may operate on a predetermined program, that is a program which varies the fluid flow and temperature in a predetermined manner over a predetermined period and the program may be altered at the controller.

In addition, the sensor 22 is provided for sensing the temperature of the body portion, i.e. shoulder 16, and through the controller is capable of varying the program of the controller to maintain the temperature of the shoulder 16 at a predetermined therapeutic temperature related to the actual temperature of the body portion.

The sensor 22 may sense the temperature of the surface of the shoulder 16 or may sense the shoulder temperature deeper inside the shoulder. Further the sensor 22 may be connected to supply an electrical signal proportional to the temperature of the shoulder directly to the fluid flow regulator 54 or to the temperature regulator 52 directly instead of to the controller 20 as shown in FIG. 1.

As indicated above, the inner and outer members 24 and 30 of the therapeutic shield 14 are preferably constructed of a flexible elastomer, such as a block copolymer and vulcanizate which is particularly flexible and has a memory property. The tubing 36, as stated, is for example one quarter inch tubing which may be made of an elastomer and again is particularly flexible.

The gel is a silicon gel and transfers cold or heat readily between the tube 36, which also readily transfers cold or heat, to the inner shield member 24 and thus to the shoulder 16 of the patient 12 to which the shield is applied.

Figure 7:
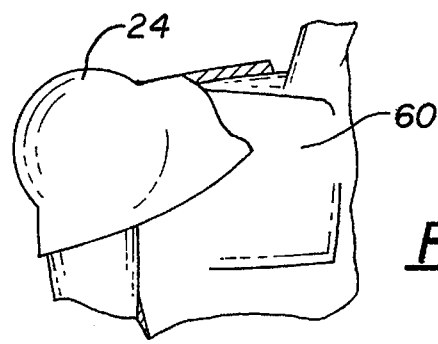
FIG. 7, is a partly broken view showing the inner member of the shield of the therapeutic device of the invention molded on the image of the body portion shown in FIG. 6.
Figure 8:
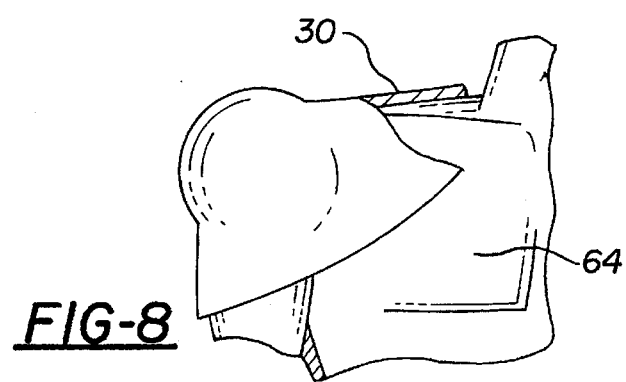
FIG. 8, is a partly broken view of the outer member of the shield of the therapeutic device of the invention molded on a slightly enlarged image of the body portion.

In construction of the shield 14 as shown in FIGS. 5–8, a cast 56 is first made of the shoulder 16 of the patient 12. The cast 56 is then removed from the patient and inverted to form the mold 50 shown in FIG. 6 into which is cast an exact replica 60 of the body portion of the patient 12, that is the shoulder 16. Subsequently, as shown in FIG. 7, an exact negative image of the form of the shoulder 16 is produced by applying the elastomer of the inner member 24 over the casting 60. A second casting 64 of the shoulder 16, which is slightly larger than the casting 60, is produced, as shown in FIG. 8, and the elastomer for the outer member 30 of the shield 14 is molded on the larger casting 64.

Alternatively, the cast 56 may be utilized, after removal from the patient, to mathematically provide electrical signals which are preferably digital which represent the cast 56 and are stored. Subsequently, the electrical signals are retrieved and used to machine or otherwise produce the castings 60 and 64 on which the inner and outer members 24 and 30 are molded. Mathematical data obtained from the cast 56 would be used to produce high volume manufacturing dies for molding the shield inner and outer members.

The tube 36 is coiled in surface to surface contact about the inner surface 32 of the outer member 30 with the ends 40 and 42 extending out of the outer member 30 as shown in FIGS. 1 and 2. The coiled tube is adhered to the outer member 30. The gelatinous substance 38 is positioned between the inner member 24 and the tube 36. The inner member 24 and outer member 30 are then sealed together around their outer periphery to form the shield 14.

The shield 14 is thus particularly adaptable to make intimate surface to surface contact with the shoulder 16 or other body portion from which it is modeled and to retain such intimate surface to surface contact with the body portion due to the inclusion of the gel in the pocket 48 formed by the inner and outer members and the weight of the shield including the fluid passing through the pocket in the tube 36. If considered desirable, on a certain body portion, shield fastening systems can be provided to maintain the shield in position on a patient.

The molded elastomeric shield 14 is thus comfortable in that it conforms exactly to the body portion and will maintain a substantially uniform temperature over the entire body portion in intimate surface to surface contact therewith in accordance with the temperature and fluid flow of the fluid flowing through the tube 36.

Alternatively, in production the inner and outer members 24 and 30 may be produced in stepped sizes or small, medium and large, petite, stout, long or short for female and male, children and adults as required to obtain the desired intimate surface to surface contact between shield 14 and a patients body portion. The production shields are preferably disposable.

As alluded to above, in use of the therapeutic device 10 of the invention, the shield 14 constructed as described above is placed on a body portion, here shoulder 16, that it is desired to maintain at a predetermined or programmed temperature or at a temperature related to the temperature of the body portion, the controller is set to provide the required temperature and fluid flow from the reservoir 50 in accordance with a programmed temperature and fluid flow as modified by the body temperature sensor 22.

With such use of the device 10, a desired therapeutic effect of temperature on an injury or after an operation, may be realized with, long or short term, close control of the temperature of the body portion to be treated. Also, additional damage to a body portion injured by a sprain or surgery may be minimized by cooling of the body portion with the device 10 before excessive swelling can occur at the sprain. Furthermore, pain can be treated over short or long periods of time by maintaining a body portion at a reduced temperature without injury to the body portion or discomfort to the patient utilizing the device 10. In addition, pain can be treated for a short period or over an extended period of time by maintaining a body portion at a reduced temperature for long periods without injury to the body part or discomfort to the patient.

Also, wherein heat therapy is desired to promote healing, the controller 20 and reservoir, fluid flow and temperature regulator 18 can provide the same type of program as heat therapy to a body portion of a patient as required.

Having thus described the therapeutic structure and methods invention in detail, it will be understood that other embodiments and modifications of the invention are contemplated by the inventor. Thus, the shield may be molded in the form of a foot, an ankle, an elbow, knee, wrist, neck, etc. Also, the casts and molds may be made by any of the molding processes of casting, rotational, injection, co-injection and lost core molding or like molding processes. Further, the invention may be used to treat animals and in industry where a manufacturing process requires a programmed temperature. It is therefore the intention to include all embodiments and modifications of the invention disclosed as are defined by the appended claims within the scope of the invention.

What is claimed is:

1. Temperature control structure for a body portion having an outer surface, comprising a shield including an inner member having an outer surface shaped at the time of manufacture to an exact mirror image of the outer surface of the body portion and having a periphery, an outer member having an inner surface and a periphery, means securing the inner and outer members together around their peripheries to form a pocket therebetween and a gelatinous substance in the pocket between the inner and outer members for holding the outer surface of the inner member in close surface to surface contact with the outer surface of the body portion the temperature of which it is desired to control, means at least partly within the pocket between the inner surface of the outer member and the gelatinous substance for regulating the temperature of the shield and means connected to the regulating means for controlling the regulated temperature of the shield.

2. Structure as set forth in claim 1, wherein the gelatinous substance is free within the pocket.

3. Structure as set forth in claim 1, wherein at least the outer surface of the inner member is molded to the exact mirror image of the outer surface of the body portion.

4. Structure as set forth in claim 1, wherein the means for regulating the temperature of the shield includes a tube having a central portion within the pocket and tube ends extending out of the pocket.

5. Structure as set forth in claim 4, wherein the central portion of the tube is coiled within the pocket in the shape of the outer surface of the body portion.

6. Structure as set forth in claim 5, wherein the coiled tube has adjacent portions within the pocket in surface to surface contact with each other.

7. Structure as set forth in claim 6, wherein the coiled tube is attached to the inner surface of the outer member of the shield.

8. Structure as set forth in claim 1, wherein the means for regulating the temperature of the shield is means for circulating a fluid through the pocket.

9. Structure as set forth in claim 8, wherein the means for regulating the temperature of the shield also includes means for regulating at least one of the parameters of the fluid.

10. Structure as set forth in claim 9, and further including means for separately sensing the temperature of the body part connected to the means for controlling wherein the controlling means is responsive to the means for sensing the temperature of the body part to control the regulator in accordance with the sensed temperature of the body part.

11. Structure as set forth in claim 10, wherein the parameter controlled is fluid flow.

12. Structure as set forth in claim 10, wherein the parameter controlled is the temperature of the fluid.

13. Structure as set forth in claim 9, wherein the parameter regulated is fluid flow.

14. Structure as set forth in claim 9, wherein the parameter regulated is the temperature of the fluid.

15. Structure as set forth in claim 1, wherein at least one of the outside and inside members is constructed of an elastomer which has a memory property which enables the one member to retain a form which is a mirror image of the body part the temperature of which it is desired to control.

16. Structure as set forth in claim 15, wherein the elastomer member is the inside member.

17. Structure as set forth in claim 16, wherein the elastomer is a block copolymer.

18. Structure as set forth in claim 16, wherein the elastomer is a vulcanite.

19. Structure as set forth in claim 1, wherein the gelatinous substance is encased in a plastic sac within the pocket.

20. Structure for therapeutic treatment of a body portion, which body portion has an outer surface, to relieve swelling and/or pain due to injury or operation and facilitate healing of wounds and incisions by exact temperature control of the body portion comprising, a shield having a molded inner member with an outer surface molded at the time of manufacture to an exact mirror image of the shape of the outer surface of the body portion and a periphery, a molded outer member having an inner surface molded to a slightly larger, mirror image of the outer surface of the body portion and a periphery, the periphery of the inner and outer shield members being heat sealed together to form a pocket therebetween, a tube having a central portion within the pocket and ends extending out of the pocket, the central portion of the tube being coiled in the shape of the mirror image of the body portion with adjacent portions of the coiled central portion of the tube being in surface to surface contact with each other, and the central portion of the tube being attached to the inner surface of the outer member of the shield within the pocket, means for circulating a fluid through the tube attached to the ends of the tube including means for exactly regulating at least the fluid flow and temperature of the fluid circulated through the tube, means connected to the regulating means for controlling the regulating means and means for exactly sensing the temperature of the body portion, the temperature of which it is desired to control, connected to the control means to exactly regulate the fluid flow and temperature of the fluid circulated through the tube in response to the sensed temperature of the body part the temperature of which it is desired to control, wherein the outside and inside members of the shield are constructed of an elastomer which has a memory property which enables it to retain the shape of the body part which promotes intimate surface to surface contact of the shield with the body part the temperature of which it is desired to control.

* * * * *